US005643332A

United States Patent [19]
Stein

[11] Patent Number: 5,643,332
[45] Date of Patent: Jul. 1, 1997

[54] ASSEMBLY FOR FUNCTIONAL ELECTRICAL STIMULATION DURING MOVEMENT

[75] Inventor: Richard B. Stein, Edmonton, Canada

[73] Assignee: Neuromotion Inc., Edmonton, Canada

[21] Appl. No.: 530,603

[22] Filed: Sep. 20, 1995

[51] Int. Cl.$^6$ .................................................. A61N 1/18
[52] U.S. Cl. ........................ 607/49; 607/115; 607/149
[58] Field of Search .............................. 607/149, 115, 607/48, 49; 128/644, 782

[56] References Cited

U.S. PATENT DOCUMENTS

| | | | |
|---|---|---|---|
| 3,083,712 | 4/1963 | Keegan, Jr. | 607/49 |
| 4,381,012 | 4/1983 | Russek | 607/149 |
| 4,432,368 | 2/1984 | Russek . | |
| 4,796,631 | 1/1989 | Grigoryev | 607/49 |
| 5,487,759 | 1/1996 | Bastyr et al. | 607/48 |

OTHER PUBLICATIONS

"Functional Electrotherapy: Stimulation of the Peroneal Nerve Synchronized with the Swing Phase of the Gait of Hemiplegic Patients"—authors W. T. Liberson, M.D., H. J. Holmquest, M.E., David Scot, R.P.T. and Margot Dow, R.P.T. —Read at the 3rd International Congress of Physical Medicine, Session on Neuromuscular Diseases, Washington, D.C., Aug. 25, 1960.

"Enhancement of Hemiplegic Patient Rehabilitation by Means of Functional Electrical Stimulation"—Authors—A. Kralj, R. Acimovic and U. Stanic, Prosthetics and Orthotics International, 1993, vol. 17, 107–114.

*Primary Examiner*—Angela D. Sykes
*Attorney, Agent, or Firm*—Millen, White, Zelano, & Branigan, P.C.

[57] ABSTRACT

The assembly comprises a band, mountable on the leg, carrying all of the components of the assembly to provide a self-contained unit. The components comprise: electrodes for stimulating a leg nerve; a V-shaped plate for conforming with the leg's tibia to reproducibly position the band so that the electrodes are located over the nerve; a tilt sensor for measuring the angular position of the lower leg; a control circuit for processing the sensor signal information and emitting pulses through the electrodes to stimulate the leg in response to phases of body movement; and a battery for supplying power to the tilt sensor, control circuit and stimulator.

2 Claims, 4 Drawing Sheets

ASSEMBLY FOR FUNCTIONAL ELECTRICAL STIMULATION DURING MOVEMENT

FIELD OF THE INVENTION

This invention relates to an electronic stimulator comprising a garment carrying fixed electrodes and means for properly positioning the garment so that the electrodes overlie a nerve to be stimulated. The garment further carries means for monitoring body movement and means for activating the electrodes at appropriate intervals to stimulate the nerve and activate dormant muscles, thereby assisting the body in making a particular movement. For example, the stimulator may be used to assist in overcoming "foot drop" affecting a person who has had a stroke.

BACKGROUND OF THE INVENTION

Functional electrical stimulation (FES) is a method for replacing function, such as walking or grasping, that is partially or completely lost after various lesions to the central nervous system, such as stroke or spinal cord injury.

One of the most common deficits in the lower leg is "foot drop". In this condition, the patient is unable to properly activate the muscles that flex the ankle, to enable the foot to clear the ground during the swing phase of walking. Instead, the foot drops and drags along the ground.

Liberson et al, in a paper entitled "Functional Electrotherapy, Stimulation of the Peroneal Nerve Synchronized with the Swing Phase of the Gait of Hemiplegic Patients" Arch. Phys. Med., 1961, 42, 101–105, first proposed using electrical stimulation to correct foot drop. The authors suggested that the stimulation be controlled by a heel sensor. When the person leaned forward and reduced heel pressure, switch contacts built into the shoe heel would open. Upon opening the switch, current would flow to electrodes positioned over the common peroneal nerve near the knee. The nerve would be stimulated and innervate muscles that flex the ankle. Upon muscle contraction, the foot would flex and clear the ground without dragging during swing. When the heel returned to the ground at the beginning of stance phase, the switch contacts would close and stimulation would be terminated.

A number of variants of the basic system have been tried over the years and some success has been attained. The commonly known prior art electronic stimulators are reviewed in an article by Kralj et al, "Enhancement of Hemiplegic Patient Rehabilitation by Means of Functional Electrical Stimulation; Prosthet, Orthot. Int., 1993, 17, 107–114.

However, the most common device fitted for people with the condition of foot drop is still an ankle-foot orthosis ("AFO"). An AFO does not involve electrical stimulation. It is a plastic brace that fits around the lower leg and holds the foot fixed, usually at an angle near 90° with respect to the long axis of the leg.

Although AFO's have several disadvantages, the electrical stimulators have not significantly replaced them because the latter have a number of drawbacks. Included among these drawbacks are:

1. that the electrical stimulators comprise a number of pieces, all of which have to be placed and connected together accurately. Carrying this out is a difficult and time-consuming chore for a patient who has likely lost some manual dexterity and who may have suffered some cognitive impairment as a result of stroke or injury. More specifically, these stimulator units typically comprise: (a) a box containing the stimulator, battery and control electronics, which have to be placed on the body or in a pocket; (b) electrodes which has to be placed accurately on the skin; (c) some garment, such as an elastic knee stocking, for supporting the electrodes in place; (d) a foot switch; and (e) wiring connecting the electronics and electrodes;
2. that the lengthy wiring is prone to breakage;
3. that the foot switch may not work reliably on all of several different surfaces such as pavement, carpet, sand, up and down ramps and the like; and
4. that some patients may not land on their heel or put little weight on it, due to spasticity or contractures in the calf muscles. These problems can lead to failure to trigger the stimulation. An alternative is to have a fixed duration of stimulation. But this may be appropriate at some speeds of walking or levels of fatigue, but not at others.

With this background in mind, I set out to design an electronic stimulator which is easy to don and doff, which automatically and accurately positions the electrodes, which incorporates sensors that more completely monitor body motion and do not require heel pressure, which uses relatively short connecting wires, and which controls stimulation in response to the stage of body motion.

In developing the invention, I have used a locating means disclosed in U.S. Pat. No. 4,431,368, issued to Russek. This patent teaches a garment carrying a member which closely conforms to the protuberance of the spine. By positioning the member over the spine, electrodes carried by the garment are automatically located accurately over nerves to be stimulated.

SUMMARY OF THE INVENTION

A stimulator in accordance with a preferred form of the present invention comprises, in combination:

a band of stretchable, breathable fabric having fastening means at its ends for securement of the band around the user's leg in the form of a ring;

anode and cathode electrodes carried by the band in a stationary or fixed condition;

locating means, carried by the band, for cooperating with the bony protuberance of the tibia, to accurately and reproducibly locate the electrodes over the nerve to be stimulated;

tilt sensor means, carried by the band, for measuring the angle of the lower segment of the leg relative to vertical in the sagittal (forward and back) plane and emitting sensors signals indicative thereof;

battery means, carried by the band, for supplying electrical current, as required; and control means, carried by the band and connected with the sensor means, electrodes and battery means, for receiving the sensor signals, processing the sensor signals to establish values indicative of the changing angularity of the limb (that is, position of the lower leg with respect to vertical) and to compare the established values with predetermined adjustable ON and OFF threshold values and initiating and terminating the emission of electrical pulses though the electrodes on respectively reaching the ON and OFF threshold values to stimulate the leg muscles in response to phases of body movement.

The band, carrying the components, is compact and thin enough to fit comfortably under pants or other clothing.

The combination of the locating means and fastening means has enabled the assembly to be easily donned with the electrodes correctly located, even when handled by an impaired user. Test trials have shown that the entire assembly can be donned or doffed in less than a minute.

The combination of the tilt sensor with the control means provides a fine degree of continuous leg position monitoring coupled with accurately initiated and terminated stimulation. The result is that stimulation can be closely related to leg position to provide an improved and refined pattern of stimulation, in comparison to prior art FES units. The device provides continuous sensory signals and turns the stimulus on and off regardless of the speed of walking.

Those skilled in the art will realize that certain of the components described can be replaced with equivalents. For example, a resilient C-shaped carrier could replace the band. Another sensor, such as an accelerometer or electric compass, could be substituted for the tilt sensor.

However, the disclosed components are certainly preferred. The elastic band provides good securement and is easily donned and doffed. The tilt sensor provides accurate information even though the user is fat or thin, walks with shoes or in bare feet and walks fast or slow on a variety of surfaces having different inclinations. The tilt sensor further is less sensitive to pathological changes such as contractures or clonus at the ankle, than is the case for a heel switch.

However, there are some individuals who produce very little tilt of the tibia after suffering a stroke, so a stimulator equipped with a tilt sensor will not be appropriate for such individuals. Also, the tilt signal does have to be processed with analog and logic circuitry for safe and reliable functioning of the stimulator during walking.

Broadly stated, the invention is a functional electrical stimulator for use on a body limb, comprising: a band, mountable on the limb, for carrying stimulator components; cathode and anode electrodes carried by the band in a fixed condition; means, carried by the band, for reproducibly positioning the band so that the electrodes are located at specified stimulation locations; sensor means, carried by the band in a fixed condition, for measuring the angular position of the limb during movement and emitting sensor signals indicative thereof; control circuit means, carried by the band and connected with the sensor means and electrodes, for receiving the sensor signals, processing the sensor signals to establish values indicative of the changing angularity of the limb and to compare the established values with predetermined adjustable ON and OFF threshold values and initiating and terminating the emissions of pulses through the electrodes when the established values reach the ON and OFF threshold values, to stimulate the limb; and battery means, carried by the band and connected with the sensor means and control circuit means, for supplying electrical power.

DESCRIPTION OF THE PREFERRED EMBODIMENT

Figure 1:
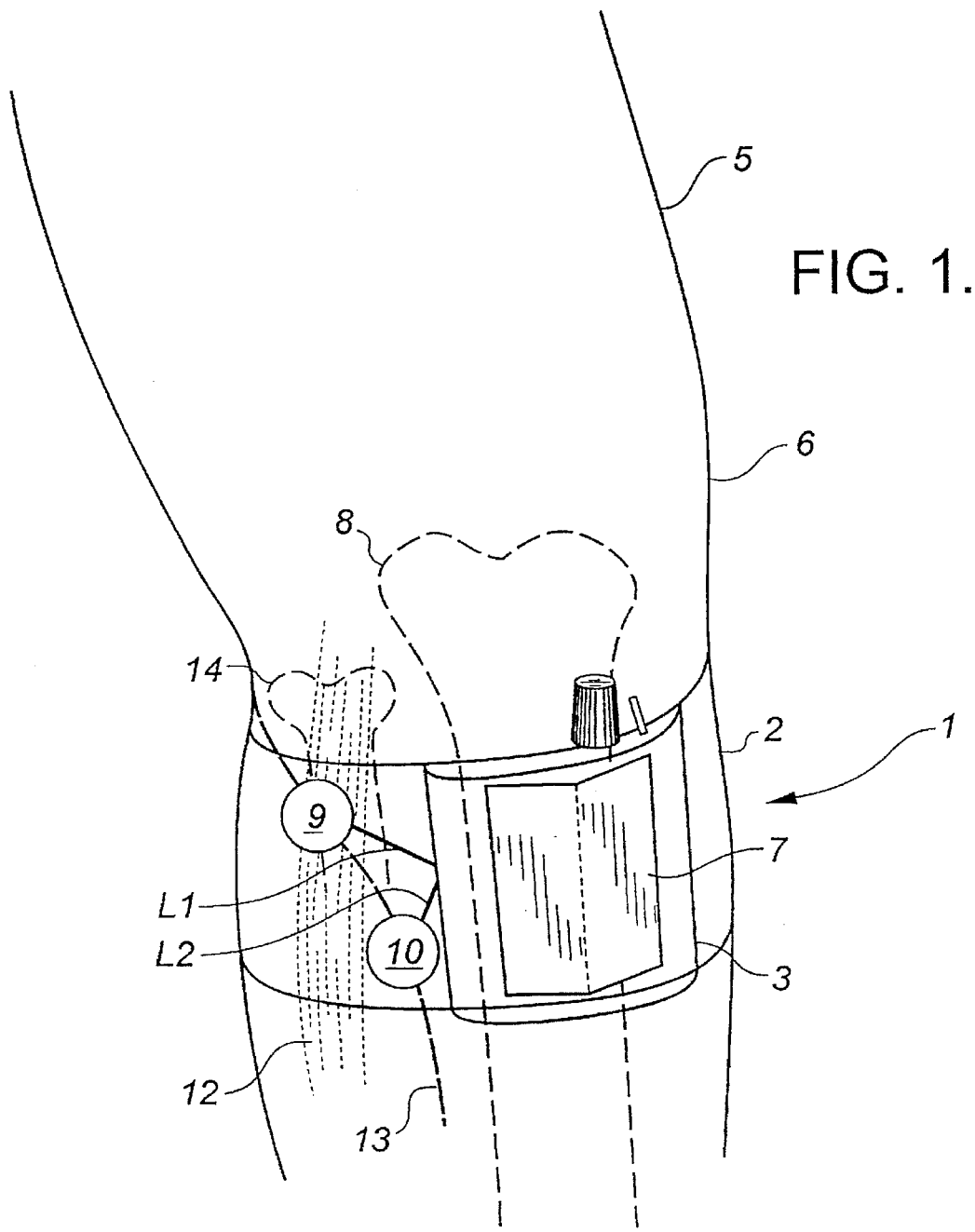
FIG. 1 is a schematic showing the stimulator mounted on a leg with the locations of the tibia and common peroneal nerve shown in dotted lines.
Figure 2:
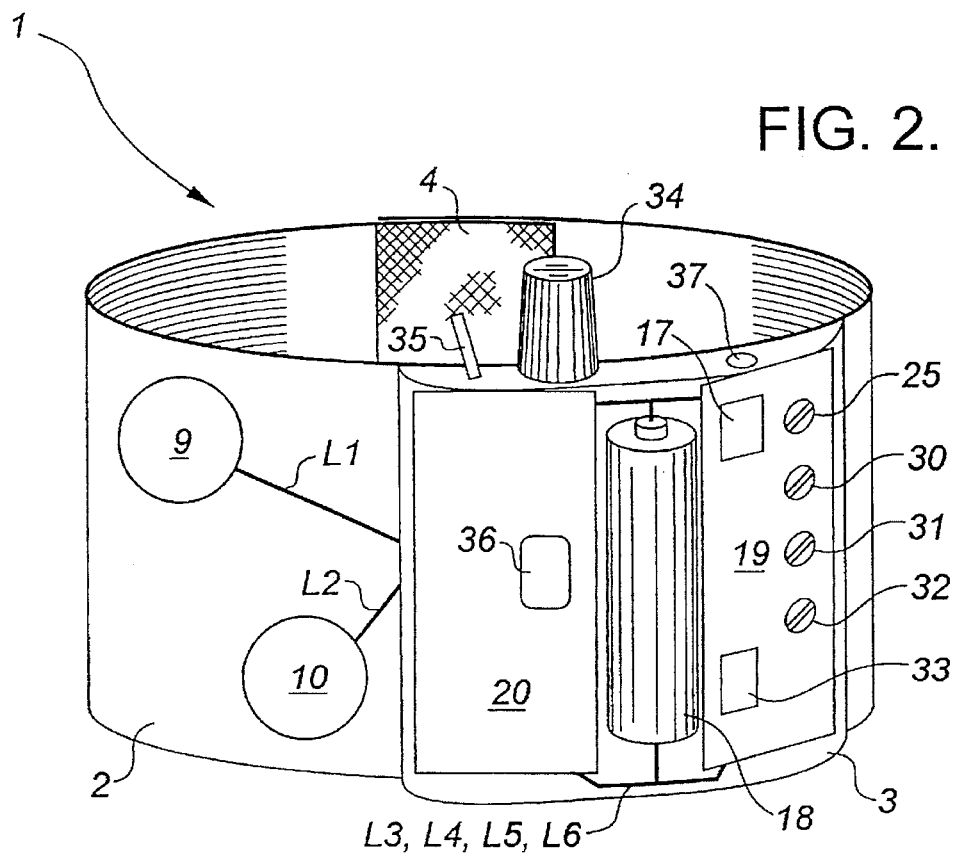
FIG. 2 is a perspective view showing the stimulator with the pouch wall broken away to display the tilt sensor, battery and circuit boards.

Having reference to FIGS. 1 and 2, the stimulator 1, comprises a band 2 made of stretchable, breathable material. One suitable material is perforated neoprene, available from Rubatex Corporation, Bedford, Va. The band 2 forms a pouch 3, for containing stimulator components. Patches 4 of Velcro* fastening material are provided at the band ends to fasten them together, so that the band can form a snug ring around the user's leg 5 below the knee 6.

*Trade Mark

A V-shaped metal plate 7 is positioned in the pouch 3 and fits snugly therein so as to be fixed along the length of the band. The plate 7 is weakened along its vertical mid-line. It can be readily bent therealong to conform to the anterior position of the tibia 8. Once so bent, the plate 7 can be located reproducibly on the tibia.

Figure 3:
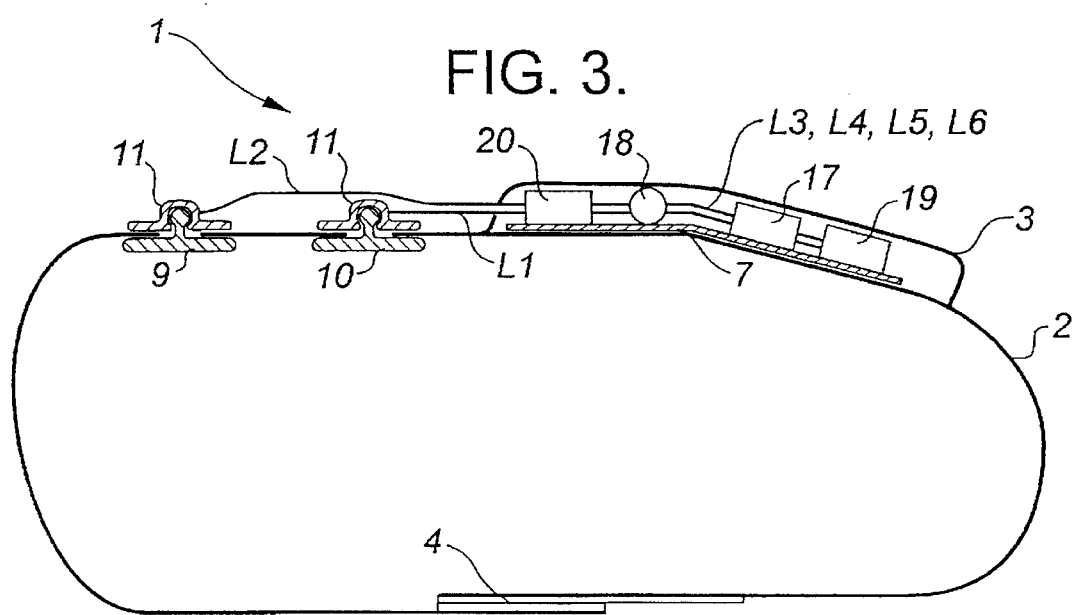
FIG. 3 is a top view of the system, showing connections between the logic circuitry, tilt sensor, battery, stimulator circuits and the electrodes.

Cathode and anode electrodes 9, 10 are attached to the band 2 with conductive snap connectors 11 as shown in FIG. 3.

The optimal placement of the electrodes 9, 10 is determined by a technician or clinician working with the patient. The cathode electrode 9 is usually placed where the common peroneal nerve 13 comes from behind the knee 6 past the head of the fibula 14. Placement of the anode electrode 10 is less critical. It is usually placed further along the course of the nerve 13, where it enters the ankle flexor muscles 12. Once these locations are determined, the band 2 is placed over the electrodes and holes are punched through the fabric with a hole punch. The electrodes contain a male connector that is fitted through the hole and connected with the female connector 11. These female connectors are attached to leads L1, L2.

The electrodes used are of the water-filled cotton type, available from the Josef Stefan Institute, Ljubljana, Slovenia.

In summary then, the band 2 is reproducibly positioned by fitting the plate 7 over the tibia 8, thereby locating the electrodes 9, 10 at the desired positions.

A tilt sensor 17 (otherwise known as an inclinometer) is secured to a printed circuit board containing logic circuit 19 which in turn is attached to the positioning plate 7. Thus, the tilt sensor is fixed with respect to the tibia and the rest of the lower leg. As previously stated, the tilt sensor 17 functions to measure the angle of the lower leg with respect to the vertical in the sagittal plane and emit signals indicative thereof. One suitable sensor for this purpose is available from Midori Inc. Fullerton, Calif., under the designation Model No. UV1.

A 1.5 V AA alkaline or 1.2 VAA NiCd battery 18 for powering the components is attached to the plate 7. The output voltage of the battery 18 is increased to 3 volts by a DC-DC converter 28, for operation of the logic circuit 19. As described below, the battery output voltage is increased to 70 volts by a transformer 29, for operation of the stimulator circuit 20.

The logic circuit 19 and stimulator circuit 20 are mounted to the plate 7 and together comprise control circuit means.

The logic circuit 19 functions to receive the tilt sensor signals, condition them, compare them to threshold values related to changes in gait and to activate or de-activate the stimulator circuit 20 in response thereto.

Figure 4:
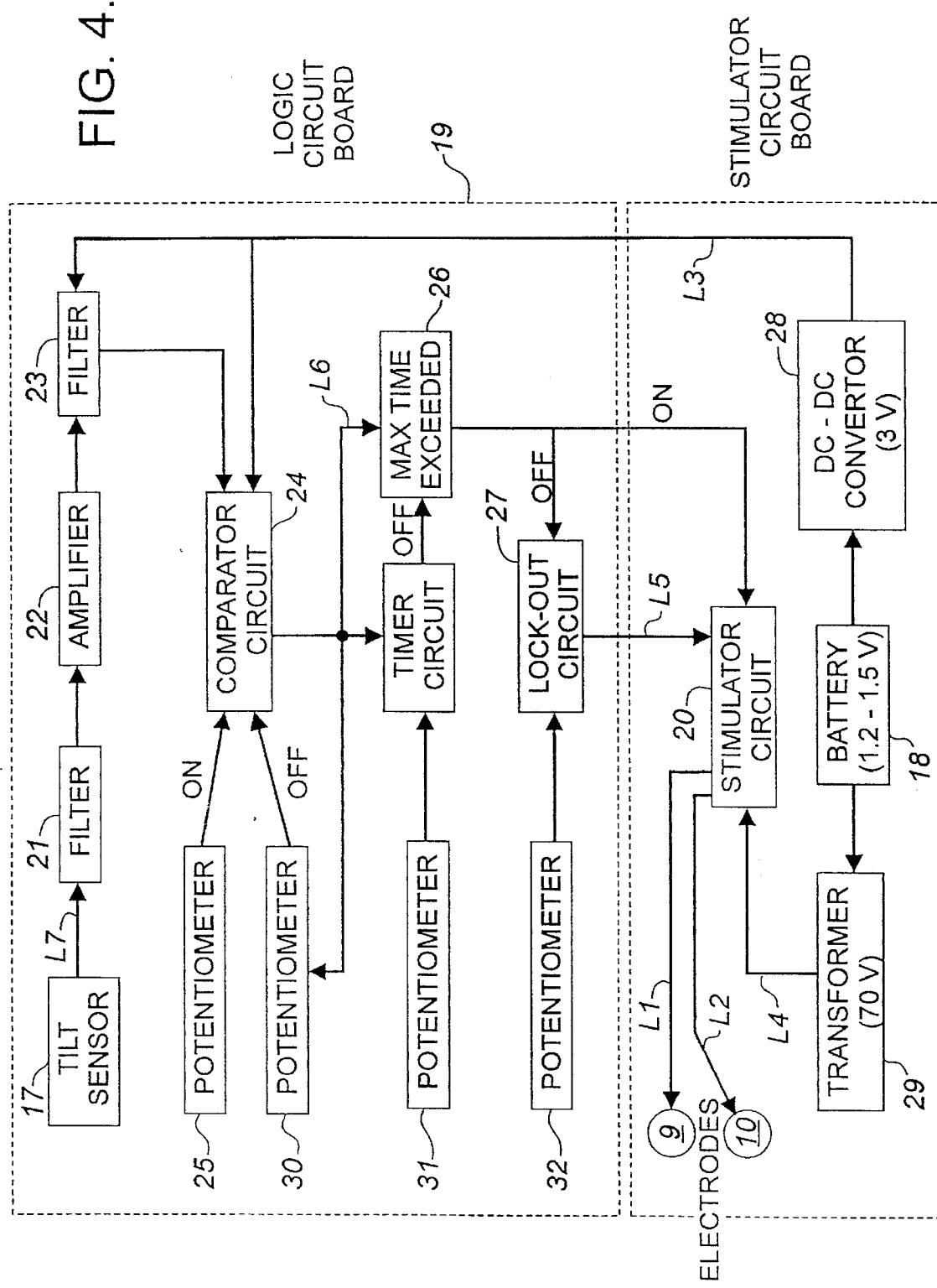
FIG. 4 is a block diagram showing the tilt sensor, logic, power and stimulator circuits and the electrodes.

As shown in FIGS. 3 and 4, the logic circuit 19 is connected by suitable leads L3-L6 with the battery 19, tilt sensor 17 and stimulator circuit 20.

For simplicity lead L3 from the DC-DC converter is only shown connected to the comparator and filter circuits in FIG. 4, but in reality it powers all elements on the logic circuit board 19.

The transformer 29 functions to increase the low voltage battery to higher voltage and the stimulation circuit 20 produces short energy pulses. It is connected with the electrodes 9, 10 by leads L1 and L2.

Turning now to describing the components and functions of the logic circuit 19.

The tilt sensor 17 produces a sensor signal of varying voltage, dependent on its position relative to gravity. This sensor signal is transmitted to the filter circuit 21 through lead L7. The signal is filtered by a standard R.C. filter circuit 21. It has values of: R=82 Kohms, C=1.0µF. The filter R.C. circuit 21 removes the higher frequency acceleration signals.

The filtered sensor signal is then amplified by operational amplifier 22. The amplifier used is available from Texas Instruments under designation TLC 274. The amplifier 22 increases the output voltage by 10 to 20 times.

The amplified sensor signal is then filtered by a second R.C. filter circuit 23, which has values of R=82 Kohms and C=1.0µF. Together the circuits 21 and 23 comprise a second-order low-pass R.C. filter with a cutoff frequency of 2 Hz.

The filtered, amplified (i.e. "conditioned") sensor signal is transmitted from filter R.C. circuit 23 to comparator circuit 24. The comparator circuit used is available from Texas Instruments under the designation TLC 274. The signal delivered is in the units of volts. The comparator circuit 24 compares the conditioned sensor signal voltage with an ON threshold and operates to activate the stimulator circuit 20 via lead L6, when the threshold is exceeded. The comparator circuit 24 also compares the conditioned sensor signal voltage with an OFF threshold and operates to deactivate or turn off the stimulator circuit 20 if the voltage drops below this threshold. Alternatively, if the voltage does not go below the OFF threshold before the maximum time set by timer circuit 26 is reached, the comparator circuit 24 operates to deactivate the stimulator circuit 20.

A potentiometer 25 enables adjustment of the ON threshold for conditioned sensor signals being transmitted to the comparator circuit 24. The potentiometer used is available from R. S. Components Ltd., Corby, Northants., U.K., under the designation 186–974.

The comparator circuit output signal is also delivered through potentiometer 30 (available from R. S. Components) to provide a variable amount of hysteresis. That is, the OFF signal will differ from the ON signal by an amount between 0 and 0.5 volts, depending on the setting of the potentiometer 30.

The comparator circuit 24 is configured to emit a HI control signal (3 volts) when the conditioned sensor signal voltage becomes greater than the ON voltage and a LOW control signal (0 volts) when the voltage becomes less than the OFF voltage.

The control signal is delivered to a timer circuit 26 and thereafter to a lock-out circuit 27. The timer circuit used is available from Motorola under designation CD4538. Once the stimulus is gated LOW, there is a further time, referred to as the lock-out period, during which the stimulus is prevented from occurring via lead L5. The lock-out circuit used is available from Motorola Semiconductor Products Inc., Austin Tex. under designation CD4538. Lock-out normally occurs at about the time that the heel strikes the ground (see FIG. 4), which gives rise to some oscillation (known as "clonus"). The combination of timer/lock-out circuits 26, 27 functions to prevent premature re-triggering of the stimulator circuit 20 due to these oscillations. The comparator circuit 24 and the timer/lock-out circuits 26, 27 thus monitor the control signals and deliver them as appropriate to the stimulator circuit 20. The timer circuit 26 is configured to allow adjustment of maximum time from 0.2 seconds to 4 seconds using the potentiometer 31 (available from R. S. Components). The lock-out time can be adjusted between 0.1 and 1 second, using the potentiometer 32 (available from R. S Components). Thus, each of the parameters—ON threshold, OFF threshold, maximum duration and lock-out period - are adjustable through the potentiometers 25, 30, 31, and 32. A socket 33 is provided in the design so that the signals can be brought from the logic circuit to a digital computer for ease of adjusting the potentiometers. Another socket 34 is also provided for connecting a hand or foot switch, since as mentioned earlier, some patients may not be able to use a tilt sensor if there is insufficient tilt of the lower leg. The circuitry for processing these signals is not novel and is not shown in FIG. 4. Essentially, inserting a hand or foot switch into the jack disables the filter and amplifier circuits and the alternative devices are connected directly to the comparator circuit 24. Choice of sensors provides flexibility to the preferred design.

The stimulator circuit 20 receives the control signal and delivers a series of stimuli (approximately 0.3 ms pulses at 40 ms intervals) though the electrodes 9, 10 for a period when the control signal remains HI. Also shown in FIG. 2 are an amplitude control 34 for adjusting the strength of the stimulus (0–100 Ma) and a switch 35 for turning the stimulator and logic circuitry on and off. A suitable stimulator circuit, for this purpose, is available from Institute Josef Stefan under designation Mikrofes Stimulator.

Figure 5:
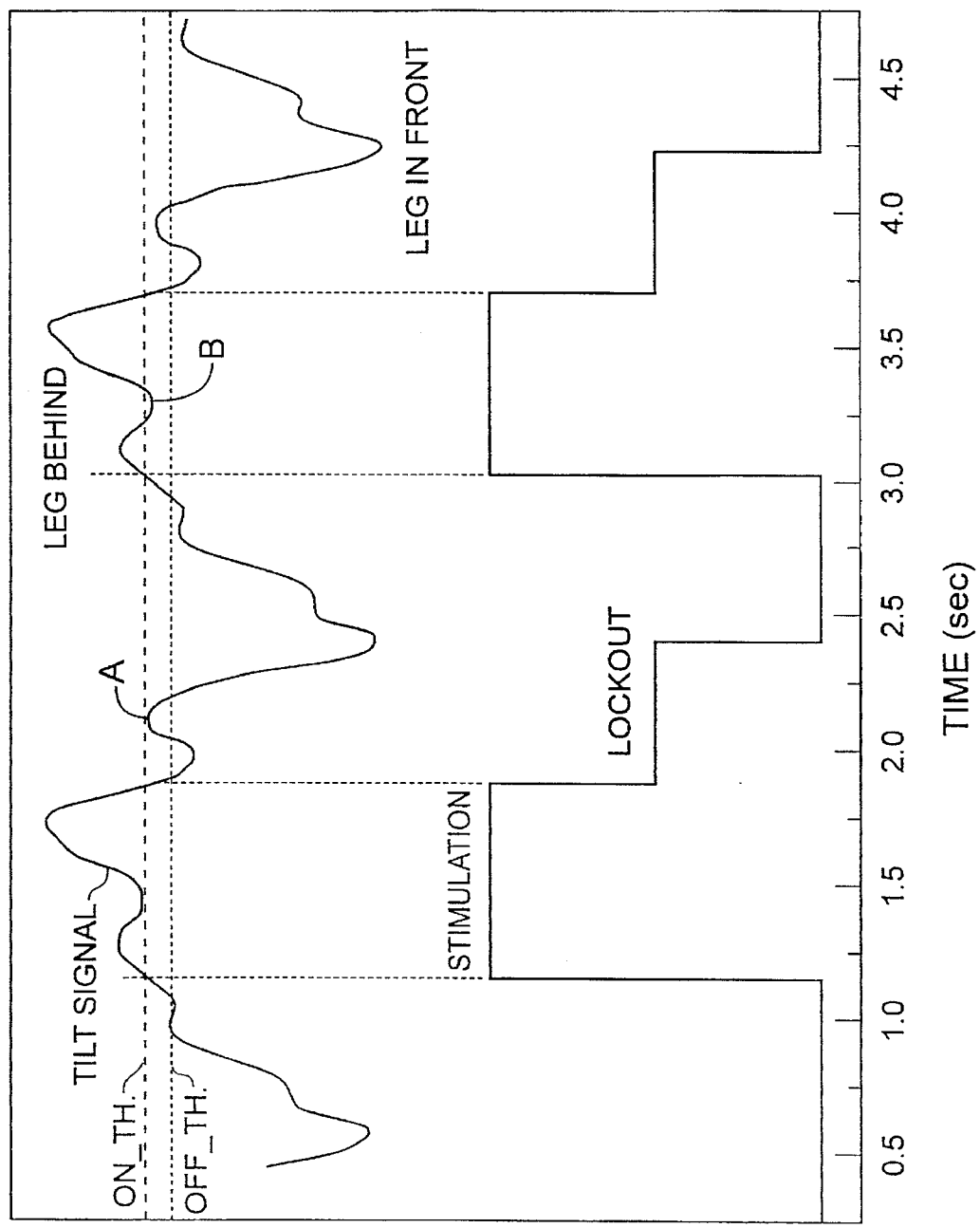
FIG. 5 is a diagram showing the operation of the logic circuitry in conjunction with data recorded from a patient user.

Reliable operation, even for persons whose movement is weak or who have considerable clonus (oscillation), is obtained as shown in FIG. 5. This Figure illustrates two complete step cycles of a person using the device described in the embodiment above. The conditional tilt signal (after amplification and filtering) is illustrated by the solid line in the top part of the Figure. It increases as the body rotates over the leg, while the leg is on the ground during the stance phase of the step cycle. When the leg is behind the body, the ON threshold is exceeded (On_Th. in FIG. 5) and stimulation begins. Stimulation continues until 1) the tilt signal falls below the OFF threshold (Off_Th. in FIG. 5), as the leg is brought in front of the body during the swing phase of the step cycle, or 2) the time set by the timer circuit 26 is exceeded (not shown in this Figure). The lockout circuit 27 prevents a subsequent retriggering of the stimulation for a period of time, even if as shown by the asterisk in the first step, oscillations in the tilt signal reach the ON threshold. The presence of hysteresis (the difference between the ON and OFF thresholds) prevents the stimulus turning off prematurely, if the stimulus falls below the ON threshold, but not the OFF threshold, as happened at the time indicated by the arrow during the second step in FIG. 5.

The embodiments of the invention in which an exclusive property or privilege is claimed are defined as follows:

1. A functional electrical stimulator for use on a body limit, comprising:
   a band, mountable on the limb, for carrying stimulator components;
   cathode and anode electrodes carried by the band in a fixed condition;
   means, carried by the band, for reproducibly positioning the band so that the electrodes are located at specified stimulation locations;

sensor means, carried by the band in a fixed condition, for measuring the angular position of the limb during movement and emitting sensor signals indicative thereof;

control circuit means, carried by the band and connected with the sensor means and electrodes, for receiving the sensor signals, processing the sensor signals to establish values indicative of the changing angularity of the limb and to compare the established values with predetermined adjustable ON and OFF threshold values and initiating and terminating the emission of pulses through the electrodes when the established values reach the ON and OFF threshold values, to stimulate the limb; and battery means carried by the band and connected with the sensor means and control circuit means, for supplying electrical power to them.

2. A functional electrical stimulator for use on a leg having a tibia and common peroneal nerve, comprising:

a band having means for fastening its ends together to mount the band around the leg;

cathode and anode electrodes carried by the band in a fixed condition;

means, carried by the band, for conforming with the tibia of the leg to reproducibly position the band so that the electrodes are located over the common peroneal nerve;

tilt sensor means, carried by the band in a fixed condition, for substantially continuously measuring the angular position of the lower segment of the leg during gait and substantially continuously emitting sensor signals indicative thereof;

control circuit means, carried by the band and connected with the sensor means and electrodes, for receiving the sensor signals, processing the sensor signals to establish values indicative of the changing angularity of the limb and to compare the established values with predetermined adjustable ON and OFF threshold values and initiating and terminating the emission of pulses through the electrodes when the established values reach the ON and OFF threshold values, to stimulate the leg; and battery means, carried by the band and connected with the tilt sensor means and control circuit means, for supplying electrical power to them.

* * * * *